United States Patent [19]

Donovan

[11] Patent Number: 6,143,306
[45] Date of Patent: Nov. 7, 2000

[54] METHODS FOR TREATING PANCREATIC DISORDERS

[75] Inventor: Stephen Donovan, Capistrano Beach, Calif.

[73] Assignee: Allergan Sales, Inc., Irvine, Calif.

[21] Appl. No.: 09/482,831

[22] Filed: Jan. 11, 2000

[51] Int. Cl.$^7$ .......................... A61K 39/02; A61K 39/08
[52] U.S. Cl. ..................... 424/236.1; 424/239.1
[58] Field of Search ............................. 424/236.1, 239.1

[56] References Cited

U.S. PATENT DOCUMENTS 5,437,291  8/1995  Pasricha et al. .................... 128/898
5,674,205  10/1997  Pasricha et al. .

OTHER PUBLICATIONS

Ahrén, B., et al.; Increased Insulin Secretion and Normalization of Glucose Tolerance by Cholinergic Agonism in High Fat–Fed Mice; *Am. J. Physiol.* 277 (Endocrinol. Metab. 40): E93–E102; (1999).

Åkesson, B., et al.; Influence of Nitric Oxide Modulators on Cholinergically Stimulated Hormone Release from Mouse Islets; *Journal of Physiology* (1999); 515.2, pp. 463–473.

Beger, H.G., et al. (Editors); *The Pancreas vol. 1* (1998); Blackwell Science Ltd.; pp. 64–67, 83–84, 109–110, and 720.

Beglinger, C.; Relevant Aspects of Physiology in Chronic Pancreatitis; *Dig. Dis.* (1992); 10:326–329.

Bilchik, A., et al.; Amelioration of Cholinergic–Induced Pancreatitis with a Selective Cholecystokinin Receptor Antagonist; *Arch. Surg.* (Dec. 1990); vol. 125, 1546–1549.

Boyd, R.S., et al.; The Effect of Botulinum Neurotoxin–B on Insulin Release from a B–Cell Line; *Movement Disorders* (1995); vol. 10, No. 3; Item 19; 376.

Boyd, R.S., et al.; The Insulin Secreting B–Cell Line HIT–15 Contains SNAP–25 Which is a Target for Botulinum Neurotoxin–A; *Movement Disorders* (1995); vol. 10, No. 3; Item 20; 376.

Brunicardi, F.C., et al., Selective Neurohormonal Interactions in Islet Cell Secretion in the Isolated Perfused Human Pancreas, *Journal of Surgical Research* (1990);48, 273–278.

Czakó, L., et al.; Pancreatic Fluid Hypersecretion in Rats After Acute Pancreatitis; *Digestive Diseases and Sciences* (Feb. 1997); vol. 42, No. 2; 265–272.

Dressel, T.D., et al.; The Effect of Atropine and Duct Decompression on the Evolution of Diazinon®–Induced Acute Canine Pancreatiti; *Ann. Surg.* (Apr. 1982); vol. 195:4; 424–434.

Fauci, A.S., et al. (Editors); *Harrison's Principles of Internal Medicine*, 14$^{th}$ Edition (1998); McGraw–Hill; 2064–2065.

Gonelle–Gispert, C., et al.; SNAP–25A AND–25B Isoforms are Both Expressed in Insulin–Secreting Cells and Can Function in Insulin Secretion; *Biochem. J.* (1999); 339:159–165.

Grönroos, J.M., et al.; Alcohol, Pancreatic Muscarinic Receptors and Acute Pancreatitis; *Exp Toxic Pathol* (1994); 45: 503–505.

Grönroos, J.M., et al.; Cholinergic Hypothesis of Alcoholic Pancreatitis; *Dig Dis* (1992); 10(1):38–45.

Kaneto, A., et al.; Effects of Vagal Stimulation on Glucagon and Insulin Secretion; *Endo* (1974); vol. 95, No. 4, 1005–1010.

Kohnert, K.D., et al.; Islet Neuronal Abnormalities Associated with Impaired Insulin Secretion in Type 2 Diabetes in the Chinese Hamster; *Regulatory Peptides 82* (1999); 71–79.

Laskawi, R., et al.; Up–to–Date Report of Botulinum Toxin Type A Treatment in Patients with Gustatory Sweating (Frey's Syndrome); *Laryngoscope* 108 (Mar. 1998); 381–384.

Ragona, R.M., et al.; Management of Parotid Sialocele with Botulinum Toxin; *Laryngoscope* 109 (Aug. 1999); 1344–1346.

Samuel, I., et al.; Bile–Pancreatic Juice Replacement Not Cholinergic– and Cholecystokinin–Receptor Blockade Reverses Acinar Cell Hyperstimulation After Bile–Pancreatic Duct Ligation; *The American Journal of Surgery* (Jan. 1996); 171(1), 207–211.

Wehrmann, T., et al.; Endoscopic Botulinum Toxin Injection into the Minor Papilla for Treatment of Idiopathic Recurrent Pancreatitis in Patients with Pancreas Divisum; *Gastrointestinal Endoscopy* (1999); vol. 50, No. 4, 545–548.

Zawalich, W.S., et al.; Time–Dependent Effects of Cholinergic Stimulation on Beta Cell Responsiveness; *Eur J Physiol* (1996); 432:589–596.

*Primary Examiner*—Frederick Krass
*Assistant Examiner*—Donna Jagoe
*Attorney, Agent, or Firm*—Martin A. Voet; Robert J. Baran

[57] ABSTRACT

A method for treating a pancreatic disorder by local administration of a neurotoxin, such as a botulinum toxin, into a cholinergic influenced, exocrine pancreas or endocrine pancreas, thereby reducing a secretion from the injected pancreatic tissue and effectively treating the pancreatic disorder.

30 Claims, No Drawings

METHODS FOR TREATING PANCREATIC DISORDERS

BACKGROUND

The present invention relates to methods for treating pancreatic disorders. In particular the present invention relates to methods for treating exocrine and endocrine pancreatic disorders by in vivo administration of a neurotoxin to the pancreas of a patient.

Exocrine Pancreas

The human pancreas is a gland comprised of both exocrine and endocrine tissues. The acinar cells of the exocrine pancreas secret digestive enzymes, for digesting ingested food. The ductal cells of the exocrine pancreas secret an electrolyte solution comprising bicarbonate for the neutralization of the acidic chyme produced in the stomach. Together the digestive enzymes and the electrolyte fluid make up the pancreatic juice which flows past the sphincter of Oddi into the duodenum via the pancreatic ducts. The exocrine pancreas can make up to three liters per day of pancreatic juice containing about 20 different enzymes and zymogens, such as amylase, lipase, trypsin and trypsinogen. The secretion of pancreatic juice is stimulated by the presence of chyme in the upper portions of the small intestine, and the precise composition of pancreatic juice appears to be influenced by the types of compounds (carbohydrate, lipid, protein, and/or nucleic acid) in the chyme. Gastric acid made by the stomach stimulates the release of secretin. Secretin in turn stimulates the secretion of a pancreatic juice rich in water and electrolytes. Gastric acid, long chain fatty acids and certain amino acids trigger the release of cholecystokinin (CCK) from the duodenum and jejunum. CCK stimulates the secretion of an enzyme rich secretion from the pancreas.

The constituents of pancreatic juice includes proteases (trypsin; chymotrypsin, carboxypolypeptidase), nucleases (RNAse and DNAse), pancreatic amylase, and lipases (pancreatic lipase, cholesterol esterase and phospholipase). Many of these enzymes, including the proteases, are initially synthesized by the acinar cells in an inactive form as zymogens. Thus trypsin is synthesized as trypsinogen, chymotrypsin as chymotypsinogen, and carboxypolypeptidase as procarboxypolypeptidase. These enzymes are activated according to a cascade, wherein, in the first step, trypsin is activated through proteolytic cleavage by the enzyme enterokinase. Trypsinogen can also be autoactivated by trypsin. Once activation has begun, the activation process proceeds rapidly. Trypsin, in turn, activates both chymotypsinogen and procarboxypolypeptidase to form their active protease counterparts.

The exocrine pancreatic enzymes are normally activated only when they enter the intestinal mucosa in order to prevent autodigestion of the pancreas. To prevent premature activation, the acinar cells also co-secrete a trypsin inhibitor that normally prevents activation of the proteolytic enzymes within the secretory cells and in the ducts of the pancreas. Inhibition of trypsin activity also prevents activation of the other proteases.

Pancreatitis is an inflammation of the pancreas and can be chronic or acute. Acute pancreatitis can be edematous or the more severe necrotizing or hemorrhagic pancreatitis. About five thousand new cases of pancreatitis occur each year in the United States and the mortality rate is about ten percent. Pancreatitis is frequently secondary to alcohol abuse or biliary tract disease. Pancreatitis can also be caused by drugs, trauma, gallstones or viral infection. One theory states that pancreatitis is due to autodigestion of the pancreas by proteolytic enzymes activated in the pancreas instead of in the intestinal lumen. Hence, pancreatitis is believed to manifest when an excess amount of trypsin saturates the supply of trypsin inhibitor. Excess trypsin can be due to underproduction of trypsin inhibitor, or the overabundance of trypsin within the cells or ducts of the pancreas. In the latter case, pancreatic trauma or blockage of a duct can lead to localized overabundance of trypsin. Under acute conditions large amounts of pancreatic zymogen secretion can pool in the damaged areas of the pancreas. If even a small amount of free trypsin is available activation of all the zymogenic proteases rapidly occurs, leading to autodigestion of the pancreas and the symptoms of acute pancreatitis. Pancreatitis can be fatal.

Some forms of acute pancreatitis, such as those triggered by excessive use of alcohol, scorpion sting, or intoxication by anti acetylcholine esterase containing insecticides, can be the result of excessive cholinergic stimulation of the exocrine cells of the pancreas. This excessive cholinergic stimulation can result from a symptomatic decrease in the number of pancreatic muscarinic acetylcholine receptors in pancreatitis. *Exp Toxicol Pathol* 1994 April; 45(8): 503–5.

Unfortunately, chronic pancreatitis is believed to be irreversible. Berger et al., *The Pancreas*, page 720, infra. In Western countries, chronic pancreatitis appears to affect predominantly men aged 25 to 50 years, most of whom are alcoholics.

There are many drawbacks and deficiencies in current therapies for pancreatitis. Treatment of acute pancreatitis can include nasogastric suction to decrease gastrin release from the stomach and thereby prevent gastric contents from entering the duodenum and stimulating pancreatic exocrine secretions. Nasogastric suction is unpleasant and can be ineffective to arrest the course of pancreatitis.

Treatment of chronic pancreatitis can be by surgical resection of from 50% to 95% of the pancreas followed by oral enzyme replacement upon alimentation, clearly a suboptimal form of therapy.

Pancreatitis can be accompanied by constriction of pancreatic ducts leading to the duodenum resulting in a deficiency of pancreatic enzymes in the intestinal lumen, referred to as pancreatic exocrine insufficiency.

Pancreatic exocrine secretion can be regulated by both hormonal and nervous mechanisms. Thus, during the gastric phase of stomach secretion, parasympathetic nerve impulses to the pancreas result in acetylcholinergic stimulation of and release of enzymes by the cholinergically innervated acinar cells.

Significantly, cholinergic innervation dominates neuronal control of the exocrine pancreas. (Berger et al., *The Pancreas*, volume 1, chapter 5, pages 65–66, Blackwell Science Ltd. (1998), which publication (two volumes) is incorporated herein by reference in its entirety) and it is known that cholinergic stimulation promotes secretion of pancreatic enzymes. Notably, pancreatic acinar cells have acetylcholine receptors. *Ibid*, pages 83–84. Extrinsic nervous control of the exocrine pancreas is parasympathetic, through vagal input. *Ibid*, page 66. Intrinsic nervous control of the pancreas refers to that part of the enteric nervous system which is within the pancreas (the intrapancreatic nervous system). The intrapancreatic nervous system comprises an interconnecting plexus of small ganglia supplied by preganglionic vagal fibers and postganglionic sympathetic fibers. Importantly, intrinsic cholinergic neurons (i.e.

those with their cell bodies in intrapancreatic ganglia) dominate in the intrapancreatic nervous system. *Ibid*, page 67.

While intravenous anticholinergics may not significantly influence exocrine pancreatic digestive fluid secretion (see e.g. *Dig Dis Sci* 1997 February; 42(2): 265–72 and *Am J Surg* 1996 January; 171(1): 207–11), extensive literature exists to support the hypothesis of significant cholinergic influence upon exocrine pancreatic cell secretory activity: See e.g. *Exp Toxicol Pathol* 1994 April; 45(8): 503–5, Dig Dis 1992;10(1):38–45, *Dig Dis* 1992;10(6): 326–9, Arch Surg 1990 December; 125(12): 1546–9, and *Ann Surg* 1982 April; 195(4): 424–34.

Endocrine Pancreas

The endocrine pancreas comprises the pancreatic islets of Langerhan which are aggregations of polypeptide hormone producing cells scattered widely throughout the acinar tissue and which are most numerous in the tail portion of the pancreas. Typically, total islet tissue constitutes only about 1 or 2 percent of the pancreatic mass.

Islet tissue contains at least three functionally different types of cells: A cells which can make glucagon, B (or β) cells which make insulin and D cells which can make a third islet hormone, somatostatin. The B cells are the most abundant of the three types of islet cells. Insulin promotes the uptake of glucose by cells, especially muscle cells and prevents an excessive breakdown of glycogen stored in liver and muscle. As an antidiabetic hormone essential for lowering blood sugar insulin is a powerful hypoglycemic agent. In most instances, the actions of glucagon are contrary to those of insulin. Thus, glucagon is a hyperglycemic factor which causes blood sugar to increase.

Glucose is the major factor which promotes release of insulin from islet B cells. Glucose also reduces glucagon secretion from islet A cells. Like glucose, glucagon (from islet A cells) also promotes insulin secretion from the islet B cells.

Endocrine pancreatic innervation of the islets of Langerhan is by both sympathetic and parasympathetic nerve fibers which terminate on or near islet cells. Notably, vagal stimulation causes the release of insulin from β cells. Berger et al., *The Pancreas*, page 110, supra. Thus, stimulation of the dorsal vagus or the pancreatic nerve increases the output of insulin and glucagon and this response is abolished by atropine, a muscarinic acetylcholine receptor antagonist. Additionally, the parasympathetic neurotransmitter acetylcholine stimulates release of insulin from B cells in vivo and in vitro.

Thus, endocrine pancreatic activity appears to be cholinergically influenced since parasympathetic innervation of islet cells can apparently increase insulin secretion, and to a lesser extent, may also increase glucagon secretion. See e.g. *Amer J. Physiol* 1999 July; 277 (1 Pt 1): E93–102, *Regul Pept* Jun. 30, 1999; 82(1–3): 71–9, *J Physiol* (Lond) Mar. 1, 1999;515 (Pt 2): 463–73, *Pflugers Arch* 1996 August; 432 (4):589–96, and *J Surg Res* 1990 April; 48(4): 273–8.

Endocrine pancreatic disorders include hypoglycemia (over utilization of glucose) resulting from hyperinsulinism. Hyperinsulinism can be due to an insulinoma. Insulinoma can include single solid tumors, microadenomatosis and islet cell hyperplasia (nesidioblastosis). Additionally, familial hyperinsulinemic hypoglycemia of infancy is due to a gain of function mutation in the sulfonylurea receptor that causes constitutitive, unregulated insulin secretion. The initial treatment for serious hyperglycemia is intravenous administration of 25–50 grams of glucose as a 50% solution. Surgery is the treatment of choice for insulinoma after use of, for example, endoscopic ultrasonography to locate the tumor. Current therapy for an insulinoma if the tumor cannot be located in the pancreas is stepwise pancreatectomy (from tail to head). Resection is stopped with an 85% pancreatectomy, even if the tumor is not found, to avoid a malabsorption problem. Unfortunately, as many as 15% of patients have persistent hypoglycemia, even after surgical resection of the pancreas. Additionally, postoperative complications include acute pancreatitis, peritonitis, fistulas, pseudocyst formation and diabetes mellitus.

Chemotherapy for insulinoma is indicated only in preparation for surgery or after failure to find the tumor at operation. Two drugs are available, diazoxide and octreotide. Unfortunately, because diazoxide has salt retaining properties, it must be accompanied by a diuretic. Additionally, chronic use of octreotide can cause nausea and diarrhea and predispose to cholelithiasis.

Botulinum Toxin

The anaerobic, gram positive bacterium Clostridium botulinum produces a potent polypeptide neurotoxin, botulinum toxin, which causes a neuroparalytic illness in humans and animals referred to as botulism. The spores of Clostridium botulinum are found in soil and can grow in improperly sterilized and sealed food containers of home based canneries, which are the cause of many of the cases of botulism. The effects of botulism typically appear 18 to 36 hours after eating the foodstuffs infected with a Clostridium botulinum culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of botulinum toxin (purified neurotoxin complex) type A is a $LD_{50}$ in mice. One unit (U) of botulinum toxin is defined as the $LD_{50}$ upon intraperitoneal injection into female Swiss Webster mice weighing 18–20 grams each. Seven immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Botulinum toxin apparently binds with high affinity to cholinergic motor neurons, is translocated into the neuron and blocks the release of acetylcholine.

Botulinum toxins have been used in clinical settings for the treatment of neuromuscular disorders characterized by hyperactive skeletal muscles. Botulinum toxin type A has been approved by the U.S. Food and Drug Administration for the treatment of blepharospasm, strabismus and hemifacial spasm. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Significantly, it is known that the cytosol of pancreatic islet B cells contains at least SNAP-25 (*Biochem J* 1;339 (pt 1): 159–65 (April 1999)), and synaptobrevin (*Mov Disord* 1995 May; 10(3): 376).

With regard to the use of a botulinum toxin to treat a pancreatic related disorder, it is known to treat a form of pancreatitis by injecting a botulinum toxin into the minor duodenal papilla (because of the proximity of the minor papilla to the pancreatic duct) to thereby relax a constricted pancreatic duct (pancreatic divisum) and increase the flow of pancreatic juice through the pancreatic duct into the duodenum. *Gastrointest Endosc* 1999 October; 50 (4): 545–548.

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

Botulinum toxin type A can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

It has been reported that botulinum toxin type A has been used in clinical settings as follows:

(1) about 75–125 units of BOTOX®[1] per intramuscular injection (multiple muscles) to treat cervical dystonia;

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

[1]Available from Allergan, Inc., of Irvine, Calif. under the tradename BOTOX®.

The success of botulinum toxin type A to treat a variety of clinical conditions has led to interest in other botulinum toxin serotypes. A study of two commercially available botulinum type A preparations (BOTOX® and Dysport®) and preparations of botulinum toxins type B and F (both obtained from Wako Chemicals, Japan) has been carried out to determine local muscle weakening efficacy, safety and antigenic potential. Botulinum toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX®(5.0 to 10.0 units/kg) or botulinum toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for botulinum toxin type B or 0.15 ng/kg for BOTOX®). Peak muscle weakness and duration were dose related for all serotypes. DAS $ED_{50}$ values (units/kg) were as follows: BOTOX®: 6.7, Dysport®: 24.7, botulinum toxin type B: 27.0 to 244.0, botulinum toxin type F: 4.3. BOTOX® had a longer duration of action than botulinum toxin type B or botulinum toxin type F. Therapeutic index values were as follows: BOTOX®: 10.5, Dysport®: 6.3, botulinum toxin type B: 3.2. Water consumption was greater in mice injected with botulinum toxin type B than with BOTOX®, although botulinum toxin type B was less effective at weakening muscles. After four months of injections 2 of 4 (where treated with 1.5 ng/kg) and 4 of 4 (where treated with 6.5 ng/kg) rabbits developed antibodies against botulinum toxin type B. In a separate study, 0 of 9 BOTOX® treated rabbits demonstrated antibodies against botulinum toxin type A. DAS results indicate relative peak potencies of botulinum toxin type A being equal to botulinum toxin type F, and botulinum toxin type F being greater than botulinum toxin type B. With regard to duration of effect, botulinum toxin type A was greater than botulinum toxin type B, and botulinum toxin type B duration of effect was greater than botulinum toxin type F. As shown by the therapeutic index values, the two commercial preparations of botulinum toxin type A (BOTOX® and Dysport®) are different. The increased water consumption behavior observed following hind limb injection of botulinum toxin type B indicates that clinically significant amounts of this serotype entered the murine systemic circulation. The results also indicate that in order to achieve efficacy comparable to botulinum toxin type A, it is necessary to increase doses of the other serotypes examined. Increased dosage can comprise safety. Furthermore, in rabbits, type B was more antigenic than was BOTOX®, possibly because of the higher protein load injected to achieve an effective dose of botulinum toxin type B.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic and most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of the heart by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and insulin, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

What is needed therefore is an effective, long lasting, non-surgical resection, non-radiotherapy therapeutic method for treating exocrine pancreatic disorders such as pancreatitis and endocrine pancreatic disorders such as hyperinsulinism.

SUMMARY

The present invention meets this need and provides an effective, non-surgical resection, relatively long term, non-radiotherapy therapeutic method for treating disorders of the pancreas, such as pancreatitis and endocrine pancreatic disorders such as hyperinsulinism.

The present invention includes within its scope a method for treating a pancreatic disorder by local administration of a neurotoxin to a pancreas, thereby treating a pancreatic disorder. Preferably, the neurotoxin is administered in an amount of between about $10^{-3}$ U/kg and about 35 U/kg. More preferably, the neurotoxin is administered in an amount of between about $10^{-2}$ U/kg and about 25 U/kg. Most preferably, the neurotoxin is administered in an amount of between about $10^{-2}$ U/kg and about 15 U/kg. In a particularly preferred embodiment of the present invention, the neurotoxin is administered in an amount of between about 1 U/kg and about 10 U/kg.

The neurotoxin can be made by a Clostridial bacterium, such as a *Clostridium botulinum, Clostridium butyricum* or *Clostridium beratti* bacterium. Additionally, the neurotoxin can be a modified neurotoxin, such as a neurotoxin has at least one of its amino acids deleted, modified or replaced, as compared to a native or wild type neurotoxin. Furthermore, the neurotoxin can be a recombinant produced neurotoxin or a derivative or fragment thereof.

The pancreatic disorder treated can be a pancreatitis or a hyperinsulinism.

Preferably, the neurotoxin used is a botulinum toxin, such as a botulinum toxin is selected from the group consisting of botulinum toxin types A, B, $C_1$, D, E, F and G. Preferably, the neurotoxin is botulinum toxin type A and the neurotoxin is locally administered by direct injection of the neurotoxin into the pancreas.

A detailed embodiment of the present invention is a method for treating a pancreatic disorder by injecting a therapeutically effective amount of a botulinum toxin into a pancreas of a human patient, thereby reducing a secretion from a pancreatic cell and treating a pancreatic disorder. The secretion treated can be an exocrine pancreas secretion and the pancreatic disorder can be a pancreatitis. Alternately, the secretion treated can be an endocrine pancreas secretion and the pancreatic disorder is hyperinsulinism and the botulinum toxin is injected into the tail of the pancreas. Preferably, the secretion treated is a cholinergic influenced secretion and the botulinum toxin used is botulinum toxin type A, although the botulinum toxin can selected from the group consisting of botulinum toxin types A, B, C, D, E, F and G.

An additional embodiment of the present invention is a method for treating a pancreatic disorder of a human patient, the method comprising the step of local administration to a cholinergic influenced pancreatic tissue of a human patient of a therapeutically effective amount of botulinum toxin type A, thereby reducing a cholinergic influenced secretion from the pancreatic tissue and treating the pancreatic disorder.

A further embodiment of the present invention is a method for treating hypoglycemic hyperinsulinism, the method comprising the step of injecting a cholinergic nervous system influenced pancreatic tissue of a human patient with a therapeutically effective amount of botulinum toxin type A, thereby reducing a cholinergic influenced insulin secretion from the pancreatic tissue and treating hypoglycemic hyperinsulinism.

A additional embodiment of the present invention is a method for treating hyperglycemic hyperglucagonism, the method comprising the step of injecting a cholinergic nervous system influenced pancreatic tissue of a human patient with a therapeutically effective amount of botulinum toxin type A, thereby reducing a cholinergic influenced glucagon secretion from the pancreatic tissue and treating hyperglycemic hyperglucagonism.

A method for treating pain associated with pancreatitis according to the present invention can be by local administration of a botulinum toxin to a pancreas of a patient, thereby reducing pain associated with pancreatitis.

Finally, the present invention also includes a method for improving patient function by local administration of a botulinum toxin to a pancreatic tissue of a human patient, thereby improving patient function as determined by improvement in one or more of the factors of reduced pain, reduced time spent in bed, improve hearing, increased ambulation, healthier attitude and a more varied lifestyle.

To summarize, the present invention includes within its scope a method for treating a pancreatic disorder by local administration of a neurotoxin to the pancreas thereby treating a pancreatic disorder. As used herein "local administration" means direct injection of the neurotoxin into the pancreas. Systemic routes of administration, such as oral and intravenous routes of administration, are excluded from the scope of the present invention.

The present invention also includes a method for treating a gland by administering to a gland a botulinum toxin thereby reducing a secretory activity of the gland, wherein the gland is the pancreas. The gland can be an excessively secreting gland and/or the gland can be influenced by the cholinergic nervous system. Additionally, the botulinum toxin can be administered by injection into the gland or into the local area of the gland.

DESCRIPTION

The present invention is based upon the discovery that a number of disorders of the pancreas can be treated by administration of a neurotoxin to the pancreas Thus, exocrine pancreatic disorders, such as pancreatitis, can be treated, according to the present invention, by local administration of a botulinum toxin to the pancreas, thereby resulting in a reduction of a secretion from a pancreatic cell.

The present invention can be used to treat pancreatitis by reducing pancreatic enzyme secretion and hence autodigestion. For example, acute pancreatitis triggered by excessive use of alcohol, scorpion sting, or intoxication by anti acetylcholine esterase containing insecticides can be due to an excessive cholinergic stimulation. The excessive cholinergic stimulation can be the result of a decrease in the number of pancreatic muscarinic acetylcholine receptors. I have discovered that pancreatitis can be effectively treated by local administration of a neurotoxin to the pancreas. Without wishing to be bound by theory, the inventor believes that this may be due to a reduction in the secretion of cholinergic innervated acinar cell digestive enzymes, with concomitant reduction of pancreatic inflammation, subsequent to injection of a neurotoxin, such as from 10 to 500 units of botulinum toxin type A, into pancreatic tissues. A significant amount of pain can accompany pancreatitis. I have discovered that the pain which accompanies pancreatitis can be effectively treated by local administration of a neurotoxin to the pancreas.

The present invention also includes within its scope treatment of endocrine pancreatic disorders. Thus, hypoglycemia due to a neoplasm, such as an insulinoma (β cell tumor) or due to hyperplasic, hypertonic or hypertrophic B cells, can be effectively treated by local administration of a neurotoxin, such as for example 10 to 500 units of botulinum toxin type A, to cholinergic, postganglionic, parasympathetic neurons which innervate the neoplasm or dysfunctional B cell. Additionally, use of a botulinum toxin as a hyperglycemic agent can act to reduce insulin secretion by normal, cholinergic innervated, β cells and thereby act to treat the hypoglycemic condition. Without wishing to be bound by theory, the botulinum toxin is believed to act by inhibiting release of acetylcholine neurotransmitter from cholinergic, postganglionic parasympathetic fibers which innervate B cells. At high doses the botulinum toxin can also act directly upon the B cells by endocytotic absorption and B cell intracellular catalysis of one or cytosolic membrane vesicle fusion proteins by the light chain of the botulinum toxin.

The present invention also includes within its scope the discovery that hyperglycemia due to excessive or unbalanced glucagon production by A cells of pancreatic islets can be effectively treated by local administration of a botulinum toxin (i.e. 10 to 500 units) to cholinergic, preganglionic, sympathetic neurons, the postganglionic fibers of which innervate the A cells. The botulinum toxin is believed to act by inhibiting release of acetylcholine neurotransmitter from the cholinergic, preganglionic sympathetic fibers.

The botulinum toxin used is administered in vivo to reduce a secretory activity of a pancreatic secretory cell. The target tissue is cholinergically innervated or susceptible to high toxin dosing such that the proteolytic light chain of the toxin is internalized by a cholinergic neuron which influences a secretory activity of a pancreatic cell.

Thus, cholinergically innervated pancreatic cells can be treated by local administration of a neurotoxin, such as a botulinum toxin. By local administration it is meant that the neurotoxin is administered directly to the pancreatic tissue to be treated.

I have discovered that a particular neurotoxin, botulinum toxin, can be used with dramatic ameliorative effect to treat a pancreatic disorder, thereby significantly superseding thereby current surgical and radiotherapy therapeutic methods with regard to such disorders. Significantly, a single administration of the botulinum toxin can substantially reduce the symptoms of pancreatitis and/or hypoglycemia for at least several months.

The route of administration and amount of botulinum toxin administered can vary widely according to the particular pancreatic disorder being treated and various patient variables including size, weight, age, disease severity and responsiveness to therapy. Method for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill). For example, to treat chronic pancreatitis, a solution of botulinum toxin type A complex can be endoscopically or intraperitoneally injected directly into the tissues of the pancreas, thereby substantially avoiding entry of the toxin into the systemic circulation.

The specific dosage appropriate for administration is readily determined by one of ordinary skill in the art according to the factor discussed above. The dosage can also depend upon the size of the pancreatic tissue mass to be treated or denervated, and the commercial preparation of the toxin. Additionally, the estimates for appropriate dosages in humans can be extrapolated from determinations of the amounts of botulinum required for effective denervation of other tissues. Thus, the amount of botulinum A to be injected is proportional to the mass and level of activity of the tissue to be treated. Generally, between about 0.01 and 35 units per kg of patient weight of a botulinum toxin, such as botulinum toxin type A, can be administered to effectively accomplish a toxin induced pancreatic tissue secretion down regulation upon administration of the neurotoxin into the pancreas. Less than about 0.01 U/kg of a botulinum toxin does not have a significant therapeutic effect upon the secretory activity of a pancreatic cell, while more than about 35 U/kg of a botulinum toxin approaches a toxic dose the neurotoxin.

Careful placement of the injection needle and a low volume of neurotoxin used prevents significant amounts of botulinum toxin from appearing systemically. A more preferred dose range is from about 0.01 U/kg to about 25 U/kg of a botulinum toxin, such as that formulated as BOTOX®. The actual amount of U/kg of a botulinum toxin to be administered depends upon factors such as the extent (mass) and level of activity of the pancreatic tissue to be treated and the administration route chosen. Botulinum toxin type A is a preferred botulinum toxin serotype for use in the methods of the present invention.

The main site of action of botulinum toxin is the neuromuscular junction where the toxin binds rapidly and prevents the release of acetylcholine. Thus, while it is known that the botulinum toxins have a binding affinity for cholinergic, pre-synaptic, peripheral motor neurons, it is quite possible that the botulinum toxins can also bind to and translocate into a wide variety of non-neuronal secretory cells, where the toxin then acts, in the known manner, as an endoprotease upon its respective secretory vessel-membrane docking protein. Because of the relatively lower affinity of the botulinum toxins for secretory cells, such as pancreatic cells, as compared to the affinity of the botulinum toxin for the cholinergic neurons which innervate pancreatic cells, the botulinum toxin can be injected into secretory or glandular tissues to provide a high local concentration of the toxin, thereby facilitating effect of the toxin upon both cholinergic neuron and directly upon pancreatic secretory cell. Thus, the present invention is applicable to the treatment of pancreatic disorders wherein the pancreatic cells have little or no cholinergic innervation.

Preferably, a neurotoxin used to practice a method within the scope of the present invention is a botulinum toxin, such as one of the serotype A, B, C, D, E, F or G botulinum toxins. Preferably, the botulinum toxin used is botulinum toxin type A, because of its high potency in humans, ready availability, and known use for the treatment of skeletal and smooth muscle disorders when locally administered by intramuscular injection.

A route for administration of a neurotoxin according to the present disclosed invention for treating a pancreatic disorder can be selected based upon criteria such as the solubility characteristics of the neurotoxin toxin chosen as well as the amount of the neurotoxin to be administered. The amount of the neurotoxin administered can vary widely according to the particular disorder being treated, its severity and other various patient variables including size, weight, age, and responsiveness to therapy. For example, the extent of the pancreatic tissue influenced is believed to be proportional to the volume of neurotoxin injected, while the quantity of the denervation is, for most dose ranges, believed to be proportional to the concentration of neurotoxin injected. Methods for determining the appropriate route of administration and dosage are generally determined on a case by case basis by the attending physician. Such determinations are routine to one of ordinary skill in the art (see for example, Harrison's Principles of Internal Medicine (1998), edited by Anthony Fauci et al., 14th edition, published by McGraw Hill).

The present invention includes within its scope the use of any neurotoxin which has a long duration therapeutic effect when locally applied to treat a pancreatic disorder of a patient. For example, neurotoxins made by any of the species of the toxin producing Clostridium bacteria, such as Clostridium botulinum, Clostridium butyricum, and Clostridium beratti can be used or adapted for use in the methods of the present invention. Additionally, all of the botulinum serotypes A, B, C, D, E, F and G can be advantageously used in the practice of the present invention, although type A is the most preferred serotype, as explained above. Practice of the present invention can provide effective relief from a symptom of a pancreatic disorder for 27 months or longer in humans.

It is known that release of insulin from permeabilized (as by electroporation) insulin secreting cells can be inhibited by a botulinum toxin. When in vitro, the cell membranes of these non-nerve cells can be permeabilized to assist introduction of a botulinum toxin into the cell's cytosol due to the lack of cell surface receptors for a botulinum toxin. Thus, botulinum toxin type B apparently inhibits insulin secretion by cleaving synaptobrevin present in the insulin secreting cell line HIT-15. Boyd R. S., et al *The Effect of Botulinum Neurotoxin-B On Insulin Release From a Beta Cell*, Mov Disord 10(3):376 (1995). It is the inventor's contention that a botulinum toxin can block the release of any vesicle mediated exocytosis from any secretory (i.e. neuronal, glandular, secretory, chromaffin) cell type, as long as the light chain of the botulinum toxin is translocated into the intracellular medium. For example, the intracellular protein SNAP-25 is widely distributed in both neuronal and non-neuronal secretory cells and botulinum toxin type A is an endopeptidase for which the specific substrate is SNAP-25. Thus, while cholinergic neurons have a high affinity acceptor for the botulinum and tetanus toxins (and are therefore more sensitive than other neurons and other cells to the inhibition of vesicle mediated exocytosis of secretory compounds), as the toxin concentration is raised, non-cholinergic sympathetic neurons, chromaffin cells and other cell types can take up a botulinum toxin and show reduced exocytosis.

Hence, by practice of the present disclosed invention, non-cholinergic nerve fibers as well as non or poorly innervated pancreatic cells can be treated by use of an appropriately higher concentration of a botulinum toxin to bring about therapeutic relief from a pancreatic disorder.

Furthermore, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assesses using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

As set forth above, I have discovered that a surprisingly effective and long lasting therapeutic effect can be achieved by local administration of a neurotoxin to the pancreas of a human patient. In its most preferred embodiment, the present invention is practiced by direct injection into the pancreas of botulinum toxin type A. It has been reported that at the neuroglandular junction, the chemical denervation effect of a botulinum toxin, such as botulinum toxin type A, has a considerably longer duration of action, i.e. 27 months vs. 3 months.

The present invention does include within its scope: (a) neurotoxin complex as well as pure neurotoxin obtained or processed by bacterial culturing, toxin extraction, concentration, preservation, freeze drying and/or reconstitution and; (b) modified or recombinant neurotoxin, that is neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made, and includes neurotoxins with one or more attached targeting moieties for a cell surface receptor present on an exocrine or endocrine pancreatic cell.

Botulinum toxins for use according to the present invention can be stored in lyophilized or vacuum dried form in containers under vacuum pressure. Prior to lyophilization the botulinum toxin can be combined with pharmaceutically acceptable excipients, stabilizers and/or carriers, such as albumin. The lyophilized or vacuum dried material can be reconstituted with saline or water.

Treatment of acute pancreatitis by nasogastric suction is no longer necessary since gastric acid released from the stomach can still enter the duodenum without being able to stimulate the botulinum toxin treated pancreas to release its normal complement of digestive fluids.

EXAMPLES

The following examples provide those of ordinary skill in the art with specific preferred methods within the scope of the present invention for carrying out the present invention and are not intended to limit the scope of what the inventors regards as their invention

Example 1

Local Administration of a Neurotoxin into the Pancreas

Local administration of a neurotoxin directly into pancreatic tissues can be accomplished by several different methods. For example, pancreatic endoscopy for diagnostic and therapeutic purposes is well known. Therapeutic pancreatic endoscopic techniques include pancreatic sphincterotomy, stricture dilation, stenting, pseudocyst drainage and endoscopic retrograde cholangiopancreatography (ERCP) which permits visualation of and treatment of the pancreatic-biliary ductal system. An endoscope used for pancreatic therapy can be modified to permit its use for direct injection of a neurotoxin, such as a botulinum toxin directly into pancreatic tissue. See for example U.S. Pat. No. 5,674,205. For the purposes of the present invention, the endoscope is moved from the oropharynx through the stomach, duodenum, and finally into the pancreatic duct, duct decompression having been carried out previously (for example by dilation or stenting), if required, to permit lodgment of the endoscope in the duct. Once so located, a hollow needle tip can be extended from the endoscope into pancreatic tissue and through which needle the neurotoxin can be injected into the pancreatic tissue.

If the pancreatic duct is not accessible or does not decompress, a percutaneous needle, imaging guided (i.e. by ultrasound or computed tomography) can also be used for transabdominal injection of a neurotoxin directly into pancreatic tissue. Thus, percutaneous needle aspiration for pancreatic biopsy is a known technique and aspiration can be reversed to accomplish the desired toxin injection.

In each of the following examples, the specific amount of a botulinum toxin administered depends upon a variety of factors to be weighed and considered within the discretion of the attending physician and in each of the examples insignificant amounts of botulinum toxin appear systemically with no significant side effects. Units of botulinum toxin injected per kilogram (U/kg) below are per kg of total patient weight. For example, 3 U/kg for a 70 kg patient calls for an injection of 210 units of the botulinum toxin.

Example 2

Treatment of Chronic Pancreatitis

A male patient age 52 is diagnosed with chronic pancreatitis, caused, for example, by alcohol use, scorpion sting, or intoxication by anti acetylcholine esterase containing insecticides. As an alternative to surgical resection, between about $10^{-3}$ U/kg and about 35 U/kg of a botulinum toxin type A preparation is injected into the pancreas (for example between about 10 units and about 500 units of BOTOX®) using one of the techniques set forth in Example 1. Within 1–7 days the symptoms of pancreatitis are alleviated. Relief lasts for at least 2–6 months during which time the patient takes oral enzyme supplements with meals.

Example 2b

Treatment of Chronic Pancreatitis

A male patient age 52 is diagnosed with chronic pancreatitis, caused, for example, by alcohol use, scorpion sting, or intoxication by anti acetylcholine esterase containing insecticides. As an alternative to surgical resection, between about 1000 units and about 40,000 units of a botulinum toxin type B, preparation is injected into the pancreas using one of the techniques set forth in Example 1. Within a few days the symptoms of pancreatitis are alleviated. Relief lasts for at least 2 months during which time the patient takes oral enzyme supplements with meals.

Example 2c

Treatment of Chronic Pancreatitis

A male patient age 52 is diagnosed with chronic pancreatitis, caused, for example, by alcohol use, scorpion sting, or intoxication by anti acetylcholine esterase containing insecticides. As an alternative to surgical resection, between about 10 and about 20,000 units of a botulinum toxin type C, D, E, F or G is injected into the pancreas using one of the techniques set forth in Example 1. Within a few days the symptoms of pancreatitis are alleviated. Relief lasts for at least 2 months during which time the patient takes oral enzyme supplements with meals.

Example 3

Treatment of Hypoglycemic Hyperinsulinism

A 62 year old female is admitted with symptoms of hypoglycemia. Biopsy reveals precancerous, hyperplasic β islet cells. Between about $10^{-3}$ U/kg and about 35 U/kg of a botulinum toxin type A preparation (for example between about 10 units and about 500 units of BOTOX®) is injected into the pancreas, using one of the techniques set forth in Example 1. Within 1–7 days the symptoms of hypoglycemia are alleviated. Relief lasts for at least 2–6 months. Intravenous glucose can be initiated prior to BOTOX® administration.

Example 3b

Treatment of Hypoglycemic Hyperinsulinism

A 62 year old female is admitted with symptoms of hypoglycemia. Biopsy reveals precancerous, hyperplasic β islet cells. Between about 1000 units and about 40,000 units of a botulinum toxin type B preparation is injected into the pancreas, using one of the techniques set forth in Example 1. Within a few days the symptoms of hypoglycemia are alleviated. Relief lasts for at least 2 months. Intravenous glucose can be initiated prior to BOTOX® administration.

Example 3c

Treatment of Hypoglycemic Hyperinsulinism

A 62 year old female is admitted with symptoms of hypoglycemia. Biopsy reveals precancerous, hyperplasic β islet cells. Between about 10 units and about 20,000 units of a botulinum toxin type C, D, E, F or G preparation is injected into the pancreas, using one of the techniques set forth in Example 1. Within a few days the symptoms of hypoglycemia are alleviated. Relief lasts for at least 2 months. Intravenous glucose can be initiated prior to BOTOX® administration.

Example 4

Treatment of Hyperglycemic Hyperglucagonism

A male aged 44 presents with symptoms of hyperglycemia, diagnosed as due to hypersecretion by islet A cells. Between about $10^{-3}$ U/kg and about 35 U/kg of a botulinum toxin type A preparation is injected into the pancreas (for example between about 10 units and about 500 units of BOTOX®) using one of the techniques set forth in Example 1. Within 1–7 days the symptoms of excessive glucagon secretion are alleviated. Relief lasts for at least 2–6 months.

Example 4b

Treatment of Hyperglycemic Hyperglucagonism

A male aged 44 presents with symptoms of hyperglycemia, diagnosed as due to hypersecretion by islet A cells. Between about 1000 units and about 40,000 units of a botulinum toxin type B preparation is injected into the pancreas using one of the techniques set forth in Example 1. Within a few days the symptoms of excessive glucagon secretion are alleviated. Relief lasts for at least 2 months.

Example 4c

Treatment of Hyperglycemic Hyperglucagonism

A male aged 44 presents with symptoms of hyperglycemia, diagnosed as due to hypersecretion by islet A cells. Between about 10 units and about 20,000 units of a botulinum toxin type C, D, E, F or G preparation is injected into the pancreas using one of the techniques set forth in Example 1. Within a few days the symptoms of excessive glucagon secretion are alleviated. Relief lasts for at least 2 months.

Methods according to the invention disclosed herein has many advantages, including the following:

(1) the invention renders unnecessary many surgical procedures for effective treatment of pancreatic disorders, including hyperplasic and hypertonic pancreatic cell disorders.

(2) systemic drug effects can be avoided by direct local application of a neurotoxin according to the present invention.

(3) the ameliorative effects of the present invention can persists for two years or longer from a single local administration of a neurotoxin as set forth herein.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local pancreatic administration methods wherein two or more neurotoxins, such as two or more botulinum toxins, are administered concurrently or consecutively. For example, botulinum toxin type A can be administered until a loss of clinical response or neutralizing antibodies develop, followed by administration of botulinum toxin type E. Alternately, a combination of any two or more of the botulinum serotypes A–G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a botulinum toxin, begins to exert its therapeutic effect.

My invention also includes within its scope the use of a neurotoxin, such as a botulinum toxin, in the preparation of a medicament for the treatment of a pancreatic disorder by local administration of the neurotoxin.

Accordingly, the spirit and scope of the following claims should not be limited to the descriptions of the preferred embodiments set forth above.

I claim:

1. A method for treating a pancreatic disorder, the method comprising the step of local administration of a neurotoxin to an endocrine pancreatic and/or exocrine pancreatic tissue, thereby treating a pancreatic disorder.

2. The method of claim 1, wherein the neurotoxin is administered in an amount of between about $10^{-3}$ U/kg and about 35 U/kg.

3. The method of claim 1, wherein the neurotoxin is administered in an amount of between about $10^{-2}$ U/kg and about 25 U/kg.

4. The method of claim 1, wherein the neurotoxin is administered in an amount of between about $10^{-2}$ U/kg and about 15 U/kg.

5. The method of claim 1, wherein the neurotoxin is administered in an amount of between about 1 U/kg and about 10 U/kg.

6. The method of claim 1, wherein the neurotoxin is made by a Clostridial bacterium.

7. The method of claim 1, wherein the neurotoxin is made by a bacterium selected from the group consisting of *Clostridium botulinum, Clostridium butyricum, Clostridium beratti*.

8. The method of claim 1, wherein the neurotoxin is a modified neurotoxin.

9. The method of claim 1, wherein the neurotoxin has at least one of its amino acids deleted, modified or replaced, as compared to a native neurotoxin.

10. The method of claim 1, wherein the neurotoxin is a recombinant produced neurotoxin or a derivative or fragment thereof.

11. The method of claim 1, wherein the pancreatic disorder is pancreatitis.

12. The method of claim 1, wherein the pancreatic disorder is hyperinsulinism.

13. The method of claim 1, wherein the neurotoxin is a botulinum toxin.

14. The method of claim 1, wherein the botulinum toxin is selected from the group consisting of botulinum toxin types A, B, $C_1$, D, E, F and G.

15. The method of claim 1, wherein the neurotoxin is botulinum toxin type A.

16. The method of claim 1, wherein the neurotoxin is locally administered by direct injection of the neurotoxin into the pancreas.

17. A method for treating a pancreatic disorder, the method comprising the step of injecting a therapeutically effective amount of a botulinum toxin into an endocrine pancreatic tissue and/or to an exocrine pancreatic tissue of a human patient, thereby reducing a secretion from a pancreatic cell and treating a pancreatic disorder.

18. The method of claim 17, wherein the secretion is an exocrine pancreas is secretion.

19. The method of claim 18, wherein a pancreatic disorder is pancreatitis.

20. The method of claim 17, wherein the secretion is an endocrine pancreas secretion.

21. The method of claim 20, wherein a pancreatic disorder is hyperinsulinism.

22. The method of claim 20, wherein the botulinum toxin is injected into the tail of the pancreas.

23. The method of claim 17, wherein the secretion is a cholinergic influenced secretion.

24. The method of claim 17, wherein the botulinum toxin is botulinum toxin type A.

25. The method of claim 17, wherein the botulinum toxin is selected from the group consisting of botulinum toxin types A, B, C, D, E, F and G.

26. A method for treating a pancreatic disorder of a human patient, the method comprising the step of local administration to a cholinergic influenced pancreatic tissue of a human patient of a therapeutically effective amount of botulinum toxin type A, thereby reducing a cholinergic influenced secretion from the pancreatic tissue and treating the pancreatic disorder.

27. A method for treating hypoglycemic hyperinsulinism, the method comprising the step of injecting a cholinergic nervous system influenced pancreatic tissue of a human patient with a therapeutically effective amount of botulinum toxin type A, thereby reducing a cholinergic influenced insulin secretion from the pancreatic tissue and treating hypoglycemic hyperinsulinism.

28. A method for treating hyperglycemic hyperglucagonism, the method comprising the step of injecting a cholinergic nervous system influenced pancreatic tissue of a human patient with a therapeutically effective amount of botulinum toxin type A, thereby reducing a cholinergic influenced glucagon secretion from the pancreatic tissue and treating hyperglycemic hyperglucagonism.

29. A method for treating pain associated with pancreatitis, the method comprising the step of local administration of a botulinum toxin to an endocrine pancreatic tissue and/or to an exocrine pancreatic tissue of a patient, thereby reducing pain associated with pancreatitis.

30. A method for improving patient function, the method comprising the step of local administration of a botulinum toxin to the endocrine and/or exocrine pancreatic tissue of a human patient, thereby improving patient function as determined by improvement in one or more of the factors of reduced pain, reduced time spent in bed, improved healing, and increased ambulation.

* * * * *